United States Patent [19]
DiSomma et al.

[11] Patent Number: 5,876,699
[45] Date of Patent: Mar. 2, 1999

[54] SUNBLOCK COMPOSITION SUITABLE FOR SENSITIVE SKIN AREAS

[76] Inventors: Joseph DiSomma, 16252 Serenade La., Huntington Beach, Calif. 92647; Gerardo M. Brion, 4134 Pine Ave., Lakewood, Calif. 90712

[21] Appl. No.: 647,475

[22] Filed: May 14, 1996

[51] Int. Cl.⁶ ............................ A61K 7/42; A61K 7/025; A61K 7/021; A61K 7/00
[52] U.S. Cl. ................................ 424/59; 424/60; 424/63; 424/64; 424/400; 424/401; 424/844; 424/847; 424/938
[58] Field of Search .................................. 424/59, 60, 63, 424/64, 400, 401, 844, 847, 938

[56] References Cited

U.S. PATENT DOCUMENTS 5,223,250  6/1993  Mitchell et al. ........................ 424/59

*Primary Examiner*—Shelley A. Dodson
*Attorney, Agent, or Firm*—Schweitzer Cornman Gross & Bondell

[57] ABSTRACT

A topical sunblock formulation for shielding skin, particularly sensitive skin areas, such as around the eyes, comprising an emulsion of micronized titanium dioxide and an organic chemical sunscreen agent encapsuled in transparent plastic spheres to give a sunblock formulation free of the negative qualities of excessive whitening due to the former and skin irritation due to the latter.

12 Claims, No Drawings

SUNBLOCK COMPOSITION SUITABLE FOR SENSITIVE SKIN AREAS

BACKGROUND OF THE INVENTION

There has been increasing concern over the upsurge in skin cancer in the United States due to excessive exposure to the sun. In particular the amount of UVA exposure (320–400 nm of the solar spectrum band) is increasing since most sunscreens effectively only block UVB radiation (290–320 nm). Users continue to stay in the sun for excessive periods without seeing any immediate harmful effects of UVA radiation which are more long term in nature.

As used in the specification, the term UV covers the ultraviolet region (290–400 nanometers (nm)) of the solar spectrum. The term infrared (IR) covers the range above 760 nm.

The goal of a successful sunscreen agent must be to protect the user from both UVA and UVB radiation with minimal side effects. This has been a particularly difficult problem when attempting to protect sensitive areas, such as the area around the eyes or lips. While chemical sunscreen compositions in the form of creams and lotions are known, they are irritating when applied to such sensitive areas. If the user avoids too close a contact with such areas, needed protection is not secured.

In addition to chemical sunscreens, the use of physical sunscreens is known in the art. Such sunscreens comprise particles of relatively physiolocially inert sunblocks or sunscreens, such as kaolin, talc, zinc oxide and titanium dioxide suspended in a cream or lotion. However, such physical sunblocks have significant disadvantages. They in general exhibit lower effectiveness in absorbing UV radiation as compared to many chemical sunblocks. When their concentration is increased to promote greater effectiveness, an undesirable white layer appears on the skin which most users find objectionable. When using such physical sunscreen compositions to protect the eyes, one may assume a "racoon like" appearance clearly in conflict with the attractive tanned look sought by the average person.

Recent modifications of conventional chemical and physical sunscreens are disclosed in U.S. Pat. No. 5,223,250 to Mitchell and Mitchnick, the relevant portions of which are hereby incorporated by reference in this specification. Column 3 of this patent describes the use of "micronized" titanium dioxide or "large surface area" particles having smaller particle diameters than conventional titanium dioxide. Such micronized titanium dioxide particles are smoother and less occlusive and thus provide a more cosmetically acceptable formulation. However, they still exhibit a low sunblock effectiveness. U.S. Pat. No. 5,223,250 also discloses an alternative sunblock formulation wherein a chemical UV additive capable of absorbing ultraviolet light radiation is incorporated into commercially available small plastic particles (0.01–100 microns) during their formation (column 10 line 42 through column 11 line 47).

SUMMARY OF THE INVENTION

The present invention provides a new cosmetically acceptable sunblock formulation comprising the best qualities of both physical and chemical sunblocks. More specifically, it comprises an emulsion comprising in combination:

(1) a minor quantity of micronized titanium dioxide, and (2) a minor quantity of an organic chemical sunscreen agent, such as a cinnamate, encapsulated in plastic particles (0.01–100 microns in diameter).

The quantity of titanium dioxide is no greater than 4.0 wt % to avoid the whitening appearance which occurs at higher concentrations. However, at such levels it is not capable of providing sufficient sunblock effect to reach SPF 15 level. The supplementary presence of the encapsulated organic chemical sunscreen agent provides the added sunscreen capable to reach this necessary level without causing irritation to sensitive areas due to its encapsulation.

DETAILED DESCRIPTION OF THE INVENTION

The broad and preferred ranges of key components are as follows, all percentages being on a weight percent basis.

Component A—dispersion of micronized titanium dioxide in water, where the former is preferably 35 to 45 wt % of component A.

Component B—dispersion of encapsulated organic sunscreen, such as octyl methoxycinnamate, in water along with other ingredients to serve as the emulsifying agent and the composition of the encapsulating agent. The organic sunscreen agent comprises 20 to 30, preferably 21.5 to 25 wt % of component B.

TABLE I

| | Relative Quantity in Final Composition, wt % | |
| --- | --- | --- |
| | Broad Range | Preferred Range |
| Component A | 1.6–13.3 | 1.6–11.6 |
| Component B | 4.5–34 | 13.6–18.0. |

TABLE II

Active Ingredients
Relative concentrations of titanium dioxide and organic sunscreen (octyl methoxycinnamate) in the final product formulation are as follows:

| | Broad Range | Preferred Range |
| --- | --- | --- |
| Titanium dioxide | 0.5–4.0 wt % | 0.5–3.5 wt % |
| Size, microns | 0.03–0.08 | 0.03–0.05 |
| Organic sunscreen agent | 1.0–7.5 wt % | 3.0–4.0 wt % |

The micronized titanium dioxide have significantly smaller diameters than conventional particles (diameters above 0.1 microns). It is typically added in the form of a dispersion of titanium dioxide in water having the compositions described above.

The micronized titanium dioxide provides UVA and infrared protection by absorption and scattering. However, its concentration in the final formulation must not exceed 4 wt % in order to avoid the undesirable whitening effect.

The encapsulated organic chemical sunscreen component is made by the process described in U.S. Pat. No. 5,223,250 which is hereby incorporated by reference (particularly columns 10 and 11). The sunscreen is incorporated into plastic particles during their formation. Suitable plastics include acrylics (methyl methacrylate), styrene polymers and copolymers with acrylics; styrene acrylonitrile polymers, polyvinylpyrrolidone (PVP), polycarbonates, methylpentene polymers, terpolymers of acrylonitrile, butadiene, styrene and allyl diglycol carbonate, etc. Particularly preferred are polyvinylpyrrolidone (PVP).

Any of the sunscreen chemical agents approved by the U.S. Government can be used in the present formulations. Typical examples of the latter are:

(1) Para-aminobenzoic acid (PABA);

(2) PABA esters, such as glyceryl PABA, amyldimethyl PABA and octyldimethyl PABA;

(3) Cinnamates, such as octyl methoxycinnamate, and cinoxate.

(4) Benzophenones, such as oxybenzone and sulisobenzone.

(5) Salicylates, such as octyl salicylate.

(6) Anthranilates, such as methyl anthranilate.

As will be further described as follows, the present invention initially proposes two phases—a water phase and an oil phase. The water phase will contain most or all of the water soluble ingredients, including the micronized titanium dioxide and organic chemical sunscreen agent, and the oil phase the oil soluble components of the present formulation, such as emollients, antioxidants, preservatives. The two phases are mixed at temperatures of 60°–90° C., preferably 80°–85° C. in the presence of a suitable emulsifying agent to give a stable suspension of the two liquid phases which normally do not dissolve in each other. Other physical sunscreens, such as zinc oxide, are difficult to formulate and can lead to emulsion instability.

Suitable emulsifying agents for the practice of the present invention are:

(1) Quaternary ammonium compounds, such as Quaternium 22, and stearakonium chloride;

(2) Polyhydric alcohol esters and ethers, such as cetyl alcohol, isopropyl lanolate, and polyglycerol oleates and stearates;

(3) Sorbitan oleates and laurates;

(4) Acrylates, such as $C_{10-30}$ alkyl acrylate polymers (sold under the Carbopol trademark);

(5) Polyglycerol pentastearate alone or in combination with sodium stearoyl lactylate (NIKKOMULESE).

As an alternative to first completely forming a water phase with all ingredients and an oil phase with all its ingredients it may be desirable to form the emulsion and then add some components to it with a further mixing and/or heating step.

In addition to the key ingredients—encapsulated chemical organic sunscreen agent, micronized titanium dioxide, emulsifying agent and water, the following components typically found in sunblock formulations may be present.

Sequestering agents, such as trisodium EDTA (ethylene diamine tetraacetic acid) and trisodium phosphate.

Preservatives, such as ethyl, methyl, butyl, propyl paraben, phenoxyethanol, and diazolidinyl urea.

Humectants, such as 1,3 butylene glycol, and propylene glycol.

Soothing agents, such as extracts of chamomile, eurphasia, and witch hazel.

Anti-irritants, such as alpha bisabolol, and allantoin.

Firming agents, such as actiphyte of witch hazel, heather or butcher's broom, hydrolyzed elastin, or collagen amino acids.

Emollients, such as squalene, polydecene, or stearyl alcohol.

These are normally added to the oil phase.

In general, each class of the above was less than 5 wt %, preferably less than 3 wt % of the overall final composition. Preservative agents are normally less than 1 wt % of the composition.

GENERAL PROCESS

The oil dispersible ingredients are combined in a suitable vessel and heated to 80°–85° C. while mixing with a Lightnin mixer, sidesweep mixer or other suitable mixer of low to medium shear. The oil dispersible ingredients may, for example, consist of polydecene, jojoba esters, squalene, vitamin E acetate, dimethicone ethylparaben and triethanolamene.

The water phase ingredients are combined in a separate vessel. For example, first the acrylates/$C_{10-30}$ alkyl acrylate crosspolymer and xanthan gum (which are the gellants) are sprinkled slowly into the water with Lightnin mixing or other source of medium speed mixing while heating to a temperature of 80°–85° C. When the gellants are completely dispersed in the water, the other water dispersible ingredients are added with mixing. The other water dispersible ingredients may consist of the botanical extracts, sequestering agents and the active agents, namely, (1) the dispersion of encapsulated organic sunscreen agent, such as octyl methoxycinnamate, and (2) the dispersion of micronized titanium dioxide.

The oil phase at temperatures of 80°–85° C. is added to the water phase at temperatures of 80°–85° C. with higher shear mixing using a homogenizer, colloid mill, turbomixer or other suitable high shear mixer.

The combined water and oil phases are mixed for about 20–30 minutes until emulsification is complete and then cooled to room temperature.

SPECIFIC EMBODIMENT

The following table illustrates a suitable dispersion of both micronized titanium dioxide in water (Component A) and encapsulated organic sunscreen agent, such as octyl methoxy cinnamate (Component B) used to prepare an emulsion ultimately containing about 3 wt % titanium dioxide and 3 wt % octyl methoxycinnamate. This emulsion also contains minor quantities of each the optional components described earlier—sequestering agents, preservatives, humectants, soothing agents, anti-irritants, emollients, and firming agents. Heat sequences occurred at 80°–85° C. while mixing in several steps until the requisite emulsification was complete.

TABLE III

| (wt % in Final Product) | Weight Per Cent in Dispersion |
|---|---|
| Component A | |
| Titanium Dioxide | 29 |
| Water | 71 |
| Component B | |
| Octyl Methoxycinnamate | 21.5 |
| Water | 53 |
| Balance of Dispersion | 25.5 |
| $C_{18-38}$ Hydroxy Stearyl Stearate | |
| Dimethicone Copolyol Beeswax | |
| PEG 100 Stearate | |
| PEG Carnauba | |
| Sorbitan Tristearate | |
| PVP/Eicosene Copolymer. | |

The sunblock formulation prepared as above had an SPF level of 15–18. It was non-irritating sunscreen to sensitive areas, such as the skin areas surrounding the eyes and did not impart a white appearance as is typical with titanium dioxide.

As an emulsion, the present formulation also serves to moisturize the skin, diminish fine lines and wrinkles and firms the skin in the eye area.

Having described the present invention, that which is sought to be protected is set forth in the following claims.

We claim:

1. A sunblock formulation for shielding sensitive skin areas from ultraviolet radiation comprising an emulsion having a combination of less than 4 weight percent micronized titanium dioxide and sufficient organic chemical sunscreen agent encapsulated in transparent plastic particles 0.01–100 microns in diameter to give requisite protection from the hazardous effects of ultraviolet radiation without causing a whitening effect on the skin.

2. The sunblock formulation of claim 1, wherein said emulsion contains 1.0–7.5 wt % of said organic chemical sunscreen agent and 0.5 to 4 wt % of said micronized titanium dioxide.

3. The sunblock formulation of claim 1, wherein said micronized titanium dioxide has a particle size of 0.03–0.08 microns.

4. The sunblock formulation of claim 1, which contains sufficient micronized titanium dioxide and organic chemical sunscreen agent to provide at least a 15 SPF protection level.

5. The sunblock formulation of claim 1, wherein said organic chemical sunscreen agent is selected from the group consisting of para-aminobenzoic acid (PABA) and esters thereof, cinnamates, benzophenones, salicyclates and anthranilates.

6. The sunblock formulation of claim 5, wherein said organic chemical sunscreen agent is octyl methoxycinnamate.

7. The sunblock formulation of claim 1, wherein said organic chemical sunscreen is encapsulated in transparent plastic particles selected from the group consisting of acrylics, styrene polymers and copolymers with acrylics, styrene acrylonitrile, polycarbonate, methylpentene, and terpolymers of acrylonitrile, butadiene, styrene and allyl diglycol carbonate.

8. The sunblock formulation of claim 7, wherein said encapsulated organic chemical sunscreen agent is selected from the group consisting of para-aminobenzoic acid (PABA) and esters thereof, cinnamates, benzophenones, salicylates and anthranilates.

9. A sunblock formulation for shielding the skin areas surrounding the eyes from ultraviolet radiation comprising an emulsion containing an effective amount but no more than 4 weight percent micronized titanium dioxide and 1.0–7.5 weight percent organic chemical sunscreen agent encapsuled in transparent plastic particles 0.01–100 microns in diameter to give at least a 15 SPF protection level against UV radiation without causing a whitening effect on the skin.

10. The sunblock formulation of claim 9, wherein said organic chemical sunscreen agent is selected from the group consisting of para-aminobenzoic acid (PABA) and esters thereof, cinnamates, benzophenones, salicyclates and anthranilates.

11. The sunblock formulation of claim 9, wherein said organic chemical sunscreen agent is octyl methoxycinnamate.

12. The sunblock formulation of claim 9, which contains 0.5–3.5 wt % of titanium dioxide having a diameter in the range of 0.03–0.05 microns, and 3.0–4.0 wt % organic chemical sunscreen agent.

* * * * *